(12) United States Patent
Barron

(10) Patent No.: US 7,491,936 B2
(45) Date of Patent: Feb. 17, 2009

(54) THERMAL IMAGING CAMERAS

(75) Inventor: Donald Robert Barron, Middlesex (GB)

(73) Assignee: Thales Optronics (Staines) Ltd., Glasgow (GB)

(*) Notice: Subject to any disclaimer, the term of this patent is extended or adjusted under 35 U.S.C. 154(b) by 0 days.

(21) Appl. No.: 11/872,375

(22) Filed: Oct. 15, 2007

(65) Prior Publication Data

US 2008/0116364 A1  May 22, 2008

Related U.S. Application Data

(63) Continuation of application No. 10/470,702, filed as application No. PCT/GB02/00397 on Jan. 30, 2002, now Pat. No. 7,282,715.

(30) Foreign Application Priority Data

Jan. 31, 2001  (GB) ................ 0102529.5

(51) Int. Cl.
*G01J 3/00* (2006.01)
(52) U.S. Cl. ................. 250/330; 250/339.01
(58) Field of Classification Search .......... 250/330
See application file for complete search history.

(56) References Cited

U.S. PATENT DOCUMENTS

| | | | |
|---|---|---|---|
| 4,783,593 A | 11/1988 | Noble | |
| 4,806,761 A | 2/1989 | Carson et al. | |
| 4,820,923 A | 4/1989 | Wellman | |
| 5,534,700 A | 7/1996 | McGlynn et al. | |
| 6,008,492 A * | 12/1999 | Slater et al. | 250/334 |
| 6,079,665 A * | 6/2000 | Nella et al. | 244/3.17 |
| 6,104,488 A | 8/2000 | LeVan | |
| 6,853,452 B1 | 2/2005 | Laufer | |
| 2003/0007254 A1 | 1/2003 | Tocci | |
| 2004/0119020 A1 | 6/2004 | Bodkin | |

FOREIGN PATENT DOCUMENTS

WO  WO 93/21548  10/1993

OTHER PUBLICATIONS

Hyvarinen, T., et al., "Direct sight imaging spectrograph: a unique add-on component brings spectral imaging to industrial applications," *Digital Solid State Cameras: Designs and Applications*, San Jose, CA, USA, (1998), 3302:165-175.

Traub, W., "Constant-dispersion grism spectrometer for channeled spectra," *Journal of the Optical Society of America*, (1990), 7:9:1779-1791.

Mooney, J., et al., High-throughput hyperspectral infrared camera, Journal of the Optical Society of America, (1997), 14:11:2951-2961.

* cited by examiner

*Primary Examiner*—David P Porta
*Assistant Examiner*—Marcus H Taningco
(74) *Attorney, Agent, or Firm*—KED & Associates, LLP

(57) ABSTRACT

A modular hyperspectral thermal camera that combines a wide field-of-view with a low erroneous recognition rate is described. The modular hyperspectral thermal camera provides such low erroneous recognition rates without any requirement for cryogenically cooling the associated optical components. The modular nature of the hyperspectral thermal camera permits easy exchange of the optical components and so provides a device that is easily calibrated and varied in resolution. In addition the modular nature allows the hyperspectral thermal camera to be readily converted to a broad band thermal camera, a full field spectrograph or a thermal bandpass filter camera, as required.

1 Claim, 3 Drawing Sheets

THERMAL IMAGING CAMERAS

This application is a continuation of U.S. application Ser. No. 10/470,702 filed Feb. 27, 2004 now U.S. Pat. No. 7,282,715 which claims priority to PCT/GB02/00397 filed Jan. 30, 2002, which claims priority to GB Patent No. 0102529.5 Filed Jan. 31, 2001, the contents of which are hereby incorporated by reference.

BACKGROUND

The present invention relates to the field of thermal imaging cameras and in particular to improvements of such cameras for detecting medium wave infrared and long wave infrared regions of the electromagnetic spectrum.

A principal application for thermal imaging cameras is the detection, recognition and subsequent identification (DRI) of objects. Present cameras are required to render to a display screen or to an "image processor" the "shape and texture" attributes of such objects and their contexts to such a quality that a human observer or an electronic substitute may perform these tasks to a high probability of success. The resolution of such devices is limited to the ability of humans, or their electronic substitute, to recognise objects from the rendering on a display screen.

When combined with the achievable performances of cameras and human observers and processors, these requirements frequently impose limits on the camera's maximum field of view to such an extent that the ranges at which the tasks of DRI can be achieved are incompatible with many applications of the camera. Within the limits of technology and those imposed by natural laws, an increase in the "task achievement range" requires a reduction in the field of view of the camera. With this narrowing field-of-view, the probability of an object being present in the field is reduced. Furthermore, any decrease in the field of view of the camera is likely to result in an increase in the area of the optical aperture with consequent impact on the cost and vulnerability of the optics and the aerodynamic performance of any aircraft on which the camera is deployed.

If the intended application requires a minimum field-of-view, then the ability of the camera to recognise objects is adversely affected and the camera has only sufficient resolving power to detect objects. Such a camera is then limited in its ability to discriminate between objects because the context will inevitably contain multiple features such as animals, heated rocks or vegetation that have the same temperature difference as that created by the genuine object. In such a situation, the application of the camera is limited by erroneous recognition.

The prior art teaches of thermal cameras characterised by a wide field-of-view and a low erroneous recognition rate. Such devices are employed for the measurements of the spectral emissivity of natural and cultural objects in the so-called Medium Waved Infrared (MWIR), between 3.2 um and 5.5 pm, and Long Wave Infrared (LWIR), 7.8, um and 11.4 um, atmospheric windows. It is known to those skilled in the art that the use of such a camera capable of measuring these attributes enhances the observer's ability to discriminate between classes of object such as trees, rocks, grasses and vehicles.

A thermal imaging camera with such a capability is known as a hyperspectral camera. Rather than observing the scene using a single waveband and presenting the image as a plane, the scene is decomposed into a number of planes representing spectral sub-bands or spectral bins. The assembly of these planes is then known as a "hyperspectral cube".

It is well known to those skilled in the art and science that such hyperspectral cameras present difficulties in achieving adequate signal to noise ratio (SNR) against objects of interest whose temperature difference relative to the background is typically only a few Celsius. In a perfect thermal imaging camera, the noise in the instrument is dominated by that from the detector. To achieve such a performance, the noise internal to the detector itself must be made extremely low. This can only be achieved in detectors sensitive to LWIR radiation by cryogenically cooling the detector. Modern detectors are integrated with a closed-cycle cooling engine which can reduce the temperature of the detector array to values lower than 80 Kelvins. When fitted with such a detector, the camera is then capable of achieving "Background Limited" thermal sensitivity. This performance level indicates that the noise in the camera is created by the random arrival of photons from all objects in the field-of-view of the detector. The photon rate, and the fluctuation thereof, are determined by the temperature of the objects. As that temperature falls, so does the noise level in the detector.

This effect is exploited in modern, high performance, infrared detectors by engineering the detector package and cooling engine to cool not only the detector array but also a "cold-shield" enclosing the detector array.

The cold-shield is pierced to allow the detector to receive the scene image-forming rays from the imaging system such as a sequence of lenses or mirrors.

Inconsiderate design of this optical system leads to an instrument whose detector is exposed not only to radiation from the scene but also to that from the interior of the camera. Contributions to this additional radiation come either from the optical elements or from the enclosure, either directly or by reflections thereof from the optical components.

If the camera design is such that spectral filtering is provided prior to this process of intrusion by stray radiation, the SNR of the instrument will be adversely affected and will not achieve that possible if both the signal and noise had been spectrally filtered.

Prior designs of hyperspectral thermal cameras have solved this problem in a number of ways. A choice between the various methods is mainly influenced by the requirements of spectral resolving power and the operating waveband. The ratio of the operating waveband to the spectral resolving power is described by the term "number of channels" or "number of spectral bins".

For a camera with only a modest number of spectral bins, a preferred method is to introduce a carousel of dielectric interference filters at the entrance window of the detector. Rotation of the carousel allows measurements of the radiation transmitted through the filter. The advantage of this method is that out-of band radiation is reflected from the filter out to the optical system and either absorbed in the camera body or reflected out of the camera. Thus, the noise from the camera optics is also filtered. Another advantage of this method is that a full spatial frame is gathered during the dwell time of the filter. The disadvantage of this method is that the behaviour of interference filters is very dependent upon the angle of arrival of rays.

Thus when used with focusing optics, the spectral bandpass of the filter is widened and the number of spectral bins is limited to less than about 8 in the LWIR band.

Higher spectral resolving power can be achieved by using a spectrally dispersive component such as a prism or a diffraction grating. The principal disadvantage of a prism instrument is that the dispersive power of prisms is relatively low so that long focal lengths and thus bulky imaging optics are required to form a usefully sized spectrum. In addition, light from the interior of the camera is uncontrolled and will increase the noise.

Thus, it is normal for such instruments optical components to be cooled to a very low temperature such that this intrusive radiation is reduced. In the very highest quality instruments it is normal to cool the entire instrument which may weigh 100 kg with a cryogenic liquid such as helium. This cooling requirement eliminates such instruments from large-scale deployment that requires maneuverability. The reflective diffraction grating has a very high dispersive power and is widely used in laboratory instruments, but these are also bulky. The oblique configuration of the instruments using reflection diffractive gratings also limits their use to optics with relatively poor light-gathering capacity and field-of-view at which high image quality is possible.

The highest spectral resolving power is achieved with an instrument using a variable optical path interferometer.

This capability is gained at the penalty of poor light gathering capacity and extreme sensitivity to relative mechanical motions of the camera components.

SUMMARY OF THE INVENTION

It is an object of the present invention is to provide a hyperspectral thermal camera that combines a wide field-of-view with a low erroneous recognition rate.

It is a further object of the present invention to provide a hyperspectral thermal camera that provides a low erroneous recognition rate without any requirement for cryogenically cooling the associated optical components.

It is yet a further object of the present invention to provide a hyperspectral thermal camera that employs a modular optical system that permits easy exchange of optical components. The easy exchange of optical components provides a device that is easily calibrated, varied in resolution, and that can be readily converted from a hyperspectral thermal camera to a broad band thermal camera, a full field spectrograph or a thermal bandpass filter camera.

According to the present invention there is provided a modular hyperspectral thermal imaging camera comprising a transmissive diffraction grating, a detector and optical components, wherein the optical components of the modular hyperspectral thermal imaging camera do not required to be cryogenically cooled.

Preferably the transmissive diffraction grating comprises a linear phase grating and a refractive substrate, characterised in that for radiation of a predetermined wavelength the induced diffraction of the linear phase grating compensates the induced refraction of the refractive substrate, such that the reference radiation passes undeviated through the transmissive diffraction grating.

Preferably the detector comprises an aperture stop, a cold shield and a photodetector array.

Preferably the aperture stop is formed by piercing the cold shield.

Alternatively the aperture stop is formed by piercing a convex mirror situated externally to the cold shield, such that the radius of curvature of the mirror is equal to its distance from the photodetector array.

Preferably the photodetector array comprises a mosaic of photodiodes.

Preferably the optical components of the hyperspectral thermal imaging camera comprises an entrance slit, an imaging lens, a collimator and a focusing lens.

Preferably the optical components are formed from materials that exhibit very low absorption coefficients.

Preferably the entrance slit is formed by a transparent piercing to air, in a highly reflective surround.

Alternatively the entrance slit is formed by a transparent piercing to a transmissive material, in a highly reflective surround.

Optionally the entrance slit surround is heated to a temperature just above the dew point of the atmosphere.

Preferably the entrance slit is located internally to the imaging lens whereby the imaging lens comprising a singlet and an air spaced doublet.

Alternatively the entrance slit is located externally to the image lens whereby the imaging lens comprises an air spaced doublet and a singlet.

Most preferably the imaging lens is designed such that the image rays are telecentric.

Optionally, a pair of mirrors are inserted allowing the detector to be illuminated by a pair of reference sources chosen to be at known operating temperatures whereby the device is calibrated.

Optionally a scanning mirror may be inserted after the entrance slit allowing the field of view of the slit to be scanned through the object field.

Preferably the collimator comprising a negative aspheric lens and a positive aspheric and diffractive hybrid lens.

Most preferably the collimator is a focal.

Preferably the focusing lens comprises a positive lens and a correcting lens. Most preferably the focussing lens is designed such that the image rays are telecentric thereby forming an image on the detector.

Optionally, a cooling jacket for the optical components is employed to enhance the signal to noise ratio of the detected image.

Most preferably all the components of the hyperspectral thermal imaging camera are easily interchangeable.

Preferably the resolution of the device may be altered by changing the transmissive diffraction grating.

According to a second aspect of the present invention there is provided a method of calibrating a modular hyperspectral thermal imaging camera comprising: 1. Inserting one or more reference mirrors within the modular hyperspectral thermal imaging camera; and 2. Illuminating a detector with one or more reference sources of known opera ting temperatures.

According to a third aspect of the present invention there is provided a method of converting a modular hyperspectral thermal imaging camera to a broad band thermal imaging camera comprising the removal of a transmissive diffraction grating associated with the modular hyperspectral thermal imaging camera.

According to a fourth aspect of the present invention there is provided a method of converting a modular hyperspectral thermal imaging camera to a full field spectrograph comprising: 1. Removing an entrance slit; and 2. Rotating a transmissive diffraction grating; associated with the modular hyperspectral thermal imaging camera.

According to a fifth aspect of the present invention there is provided a method of converting a modular hyperspectral thermal imaging camera to a thermal bandpass filter camera comprising the insertion of a bandpass filter prior to the detector associated with the modular hyperspectral thermal imaging camera.

BRIEF DESCRIPTION OF THE DRAWINGS

Embodiments of the present invention will now be described, by way of example only, with reference to the accompanying drawings, in which.

DESCRIPTION OF PREFERRED EMBODIMENTS

Figure 1:
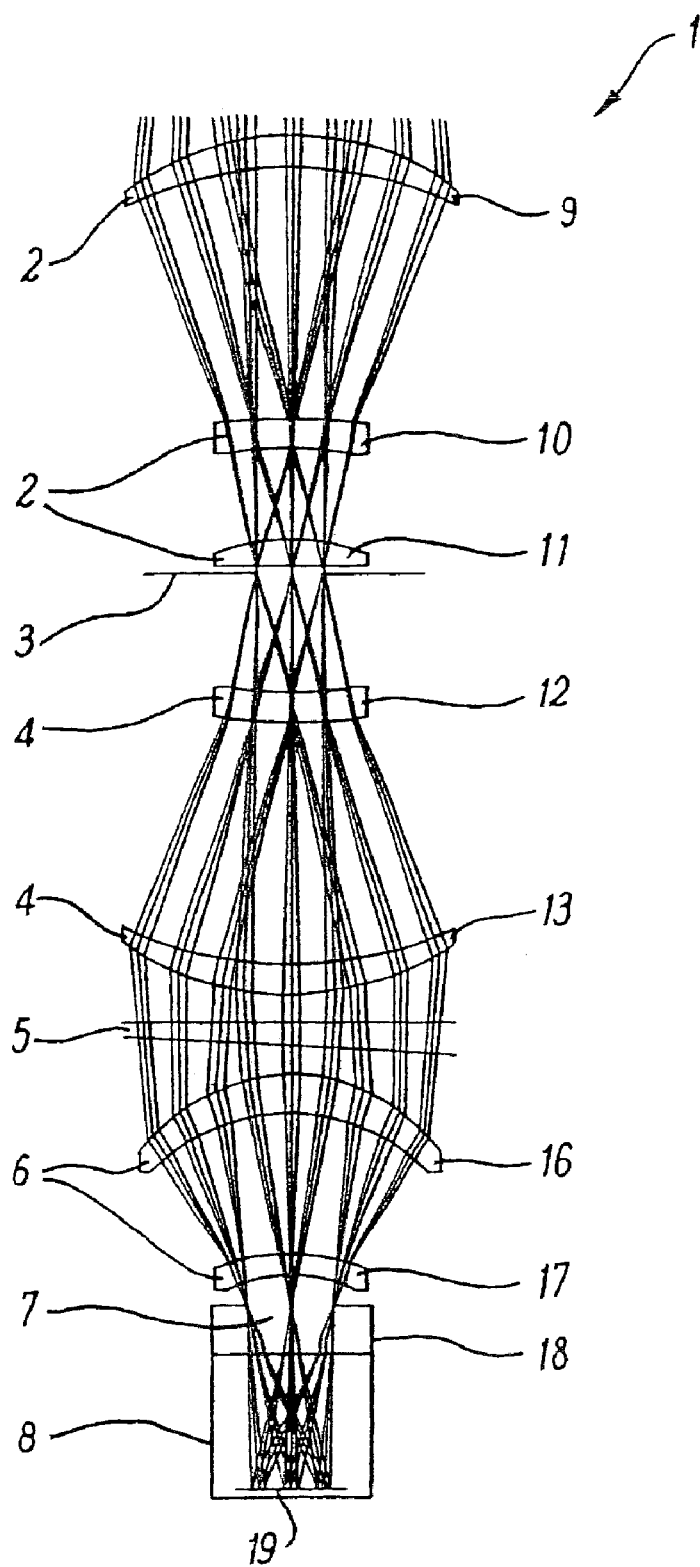
FIG. 1 illustrates a schematic presentation of a hyperspectral thermal imaging camera.

Referring initially to FIG. 1 a hyperspectral thermal imaging camera 1 can be seen to comprise of an imaging lens 2, an entrance slit 3, an afocal collimator 4, a grism 5, a focusing lens 6, an aperture stop 7 and a detector 8.

The imaging lens 2 comprises a sequence of three individual lens elements, namely a Gallium Arsenide (GaAs) lens 9, a Zinc Selenide (ZnSe) lens 10 and a Thallium Bromo Iodide lens (KRS-5) 11. These individual lenses are arranged so as to form an imaging lens whose optical performance in the infrared waveband, 8 to 11 m, is essentially limited by diffraction at the aperture stop 7.

The materials chosen for the imaging lens 2 are characterised in that they exhibit low to negligible absorption, and thus emission, of radiation in the operating waveband. Furthermore the performance of the refractive index properties of these lenses are substantially independent of variations in temperature.

The design of the imaging lens 2 is such that the image rays are telecentric with the majority of the energy contained within the slit width over the full wavelength band and over the full image height. A result of these properties is that it is not necessary to provide a focus control to ensure that the image of the object scene remains perfectly focussed at the detector 8.

The entrance slit 3 is formed by a transparent piercing in a highly reflective surround. In this embodiment the piercing is to air however, it could be to a transmissive material with or without a curved surface e.g. a lens component of the imaging lens 2. The use of a conducting transparent material such as Gallium Arsenide allows the slit surround to be heated to a temperature just above that of the dew point local to the hyperspectral thermal imaging camera 1. Thus the critical optics units may be cooled substantially without atmospheric water condensing at the entrance slit 3.

Employing Gallium Arsenide for the entrance slit surround has a further advantage in that it greatly reduces the amount of radiation energy from the slit surround tailing on the detector 8. This has the effect of avoiding an increase in the noise in the signal received at the detector 8.

The a focal collimator 4 comprises a negative Zinc Selenide lens 12 and a positive Gallium Arsenide lens 13.

The negative lens 12 is aspheric while the positive lens 13 is an aspheric and a diffractive hybrid lens. This combination of a negative 12 and positive lens 13 provides an afocal collimator 4 that exhibits telecentric properties.

Figure 2:
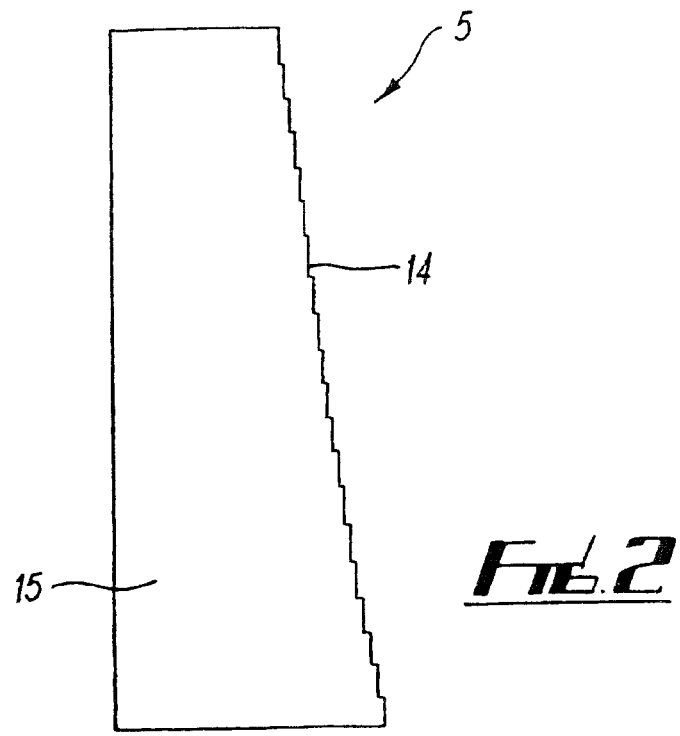
FIG. 2 illustrates a schematic presentation of a grism of the hyperspectral thermal imaging camera of FIG. 1.

FIG. 2 shows a schematic representation of the grism 5.

This is an optical element comprising a linear phase grating 14 cut on the surface of a refractive prism 15. It is characterised in that only a predetermined reference wavelength passes undeviated through the grism 5. The undeviated wavelength is that which is twice the optical step height of the linear phase grating 14, where the optical step height is a function of the geometrical height of the step and the refractive index of the substrate refractive prism 15. The spacing between the steps of the linear phase grating 14 determines the angle through which an incoming wavefront is diffracted.

The focusing lens 6 comprises a Gallium Arsenide positive lens 16 and a Zinc Selenide corrector 17. The focusing lens 6 is designed such that the image is telecentric with respect to the detector 8.

The detector 8 comprises a cryogenic cold shield 18 and a photodetector array 19. The hyperspectral thermal imaging camera 1 is designed such that the photodetector array 19 is situated at the focal plane of the device.

The aperture stop 7 is formed by piercing the cold shield 18.

The photodetector array 19 is made up of a mosaic of photodiodes. The photosensitive material is Cadmium Mercury Telluride cooled by a closed cycle thermodynamic engine to a temperature of around 70 Kelvin. The signals from the array are then stored in capacitors (not shown) connected to a silicon multiplexer (not shown) whose outputs are arranged to display a visible reconstruction of the thermal radiation from the scene pixels.

This hyperspectral thermal imaging camera 1 exploits the properties of the grism 5 such that it is able to filter out background noise without the need for cryogenic cooling of the major optical components, as is the case with the prior art. Such cooling is still required to be employed at the photodetector array 19. Incident radiation is focused by the imaging lens 2 onto the entrance slit 3. This incident radiation is then afocally imaged by the afocal collimator before being diffracted, and hence resolved, into spectral components by the grism 5. The focusing lens 6 then gathers the diffracted radiation and focuses it at the photodetector array 19. Thus, a chromatic image of the radiation at the entrance slit 3 appears at the photodetector array 19 where it can be read or subsequently displayed or processed.

The distribution of power and aberration through the lenses within the hyperspectral thermal imaging camera 1 is arranged such that the principal and marginal rays directed from the entrance slit 3 towards the detector 8 are sensibly normal to the first surfaces of the intervening lens elements. This arrangement minimises the visibility of the enclosure of the hyperspectral thermal imaging camera 1 via reflections in the lens surfaces.

The hyperspectral thermal imaging camera 1 not only images directly the radiation passing through the entrance slit 3 but also the radiation from the entrance slit surround. However, the careful design of optics within the hyperspectral thermal imaging camera 1 are such that the intensity of stray radiation incident on the photodetector array 19, and thus the background noise, is reduced to a level that is less than 10% of that which would be received from a black body at the temperature of the enclosure.

It is possible to reduce this background noise level still further by housing the hyperspectral thermal imaging camera 1 in a cooling jacket (not shown). Such a cooling jacket requires only modest cooling in order to improve the signal to noise ratio of the device, thus still avoiding the need for further cryogenic cooling.

The modular design of the hyperspectral thermal imaging camera 1 permits the quick and easy interchange of the components. For example the grism 5 may be easily substituted by another exhibiting either lower or higher spectral resolution at the focal plane. Alternatively, it is possible to remove the grism 5 entirely allowing the device to act as a broad band thermal imaging camera.

The image quality of the imaging lens 2 and the afocal collimator 4 are such that with the entrance slit 3 removed and by rotating the grism 5 about its optical axis the device operates as a full field spectrograph. A chromatic spectral cube of the two dimensional scene is obtained on the detector array 19 such that appropriate electronic processing provides a reconstruction of the scene spectral planes.

Figure 3:
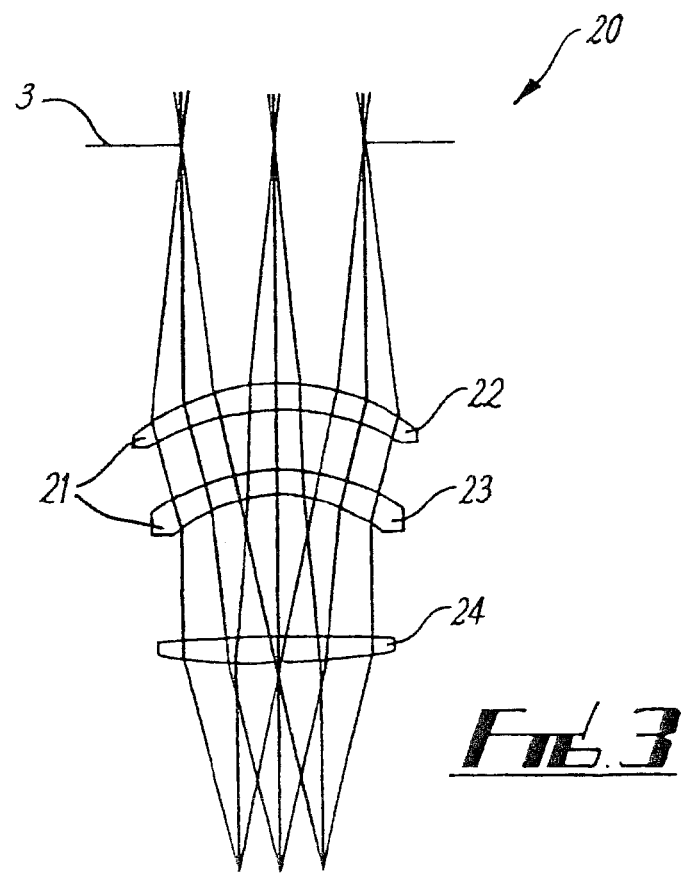
FIG. 3 illustrates a schematic presentation of an alternative focussing lens of the hyperspectral thermal imaging camera of FIG. 1.

Replacing the imaging lens 2 with an alternative embodiment imaging lens 20, as shown in FIG. 3, makes it possible to arrange the components such that the entrance slit 3 is external to the imaging lens 20. The imaging lens 20 is a Petzval type arrangement comprising an air spaced doublet 21, formed from a Gallium Arsenide (GaAs) lens 22 and a Zinc Selenide (ZnSe) lens 23 and Thallium Bromo Iodide (KRS-5) singlet 24. The airspace between the imaging lens 20 and the afocal collimator 4 is such that switch mirrors (not shown) may be inserted to allow easy calibration of the hyperspectral thermal imaging camera 1.

With this optical configuration the hyperspectral thermal imaging camera 1 is such that the entrance slit 3 is substantially ahead of the first optical element. As a result a scanning mirror (not shown) may be easily inserted so allowing the field of view of the slit through the object field to be scanned.

Figure 4:
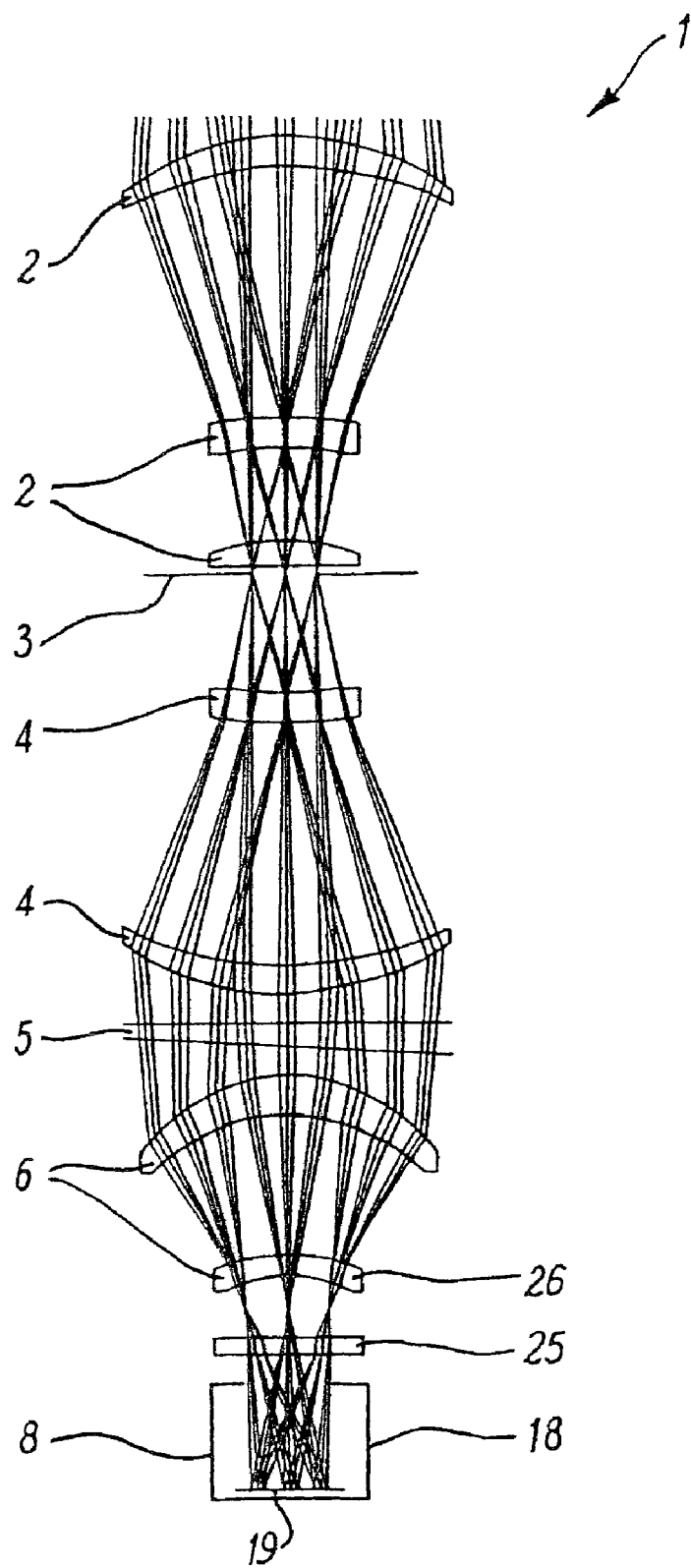
FIG. 4 illustrates an alternative embodiment of the hyperspectral thermal imaging camera of FIG. 1.

An alternative embodiment of the hyperspectral thermal imaging camera is shown in FIG. 4. In this embodiment a bandpass filter 25 is located just prior to the detector 8. The aperture stop is now formed by piercing a highly reflective mirror substrate 26 whose mirrored side is spherically centred at the centre of the detector array. In this embodiment the reflective mirror substrate 26, and hence the aperture stop, is external to the cryogenic detector enclosure.

Positioning of bandpass filters 25 in a carousel wheel (not shown) allows the spectral pass band to be selected.

Therefore in this embodiment the hyperspectral thermal imaging camera operates as a thermal bandpass filter camera that does not requite cryogenic cooling to achieve an efficient signal to noise ratio.

The design of the hyperspectral thermal imaging camera has the advantage that it removes the need to cryogenically cool the optical components in order to achieve a workable signal to noise ratio.

It is a further advantage of the invention that its modular nature allows its components to be easily exchanged. Therefore the invention can be easily altered between a hyperspectral thermal imaging camera, a broad band thermal camera, a full field thermal spectrograph, or a bandpass filter thermal camera.

A further advantage of the invention is that is applicable to both the MWIR and the LWIR wavebands using the same materials.

A yet further advantage of the invention is that the overall angular resolution or spectral resolving power of the camera may be changed by replacement of the grism.

Further advantages of the present invention are that the optics naturally provide a means for internal calibration and compensation for the temperature "gain" and "offset" errors that are unavoidable with MWIR and LWIR detectors.

Further modifications and improvements may be added without departing from the scope of the invention herein intended.

The invention claimed is:

1. A method of converting a modular hyperspectral thermal imaging camera to a full field spectrograph, comprising:
    removing an entrance slit; and
    rotating a transmissive diffraction grating associated with the modular hyperspectral thermal imaging camera.

\* \* \* \* \*